(12) United States Patent
Abbas et al.

(10) Patent No.: US 12,134,763 B2
(45) Date of Patent: *Nov. 5, 2024

(54) SYSTEM AND METHOD FOR EXTRACTING ETHANOL FROM A FERMENTATION BROTH

(71) Applicant: Archer-Daniels-Midland Company, Decatur, IL (US)

(72) Inventors: Charles Abbas, Champaign, IL (US); Dan Fanselow, White Bear Lake, MN (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 1007 days.

This patent is subject to a terminal disclaimer.

(21) Appl. No.: 16/930,607

(22) Filed: Jul. 16, 2020

(65) Prior Publication Data

US 2020/0347343 A1   Nov. 5, 2020

Related U.S. Application Data

(62) Division of application No. 15/325,557, filed as application No. PCT/US2015/039849 on Jul. 10, 2015, now Pat. No. 10,752,875.

(60) Provisional application No. 62/023,467, filed on Jul. 11, 2014.

(51) Int. Cl.
*C12P 7/06* (2006.01)
*C12M 1/00* (2006.01)
*C12M 1/26* (2006.01)
*C12M 1/34* (2006.01)
*C12M 3/00* (2006.01)
*C12P 7/14* (2006.01)

(52) U.S. Cl.
CPC .......... *C12M 47/10* (2013.01); *C12M 23/44* (2013.01); *C12M 29/14* (2013.01); *C12M 29/18* (2013.01); *C12M 33/12* (2013.01); *C12M 33/14* (2013.01); *C12M 41/34* (2013.01); *C12M 47/12* (2013.01); *C12P 7/06* (2013.01); *C12P 7/14* (2013.01); *Y02E 50/10* (2013.01)

(58) Field of Classification Search
CPC ................................. C12P 7/06; C12P 7/065
See application file for complete search history.

(56) References Cited

U.S. PATENT DOCUMENTS 10,752,875 B2 * 8/2020 Abbas .................... C12M 47/12

* cited by examiner

*Primary Examiner* — Tekchand Saidha
(74) *Attorney, Agent, or Firm* — Andrew F. Nilles

(57) ABSTRACT

The present invention is directed to a system and method for producing an organic compound using fermentation wherein multiple components of the system are recycled within the system. The system and method allow for extraction of a high concentration of the organic compound from the fermentation broth in a continuous system that allows recycling of the biomass, aqueous fermentation broth and extraction solvents. The system and method are particularly well adapted for producing and extracting ethanol.

11 Claims, 1 Drawing Sheet

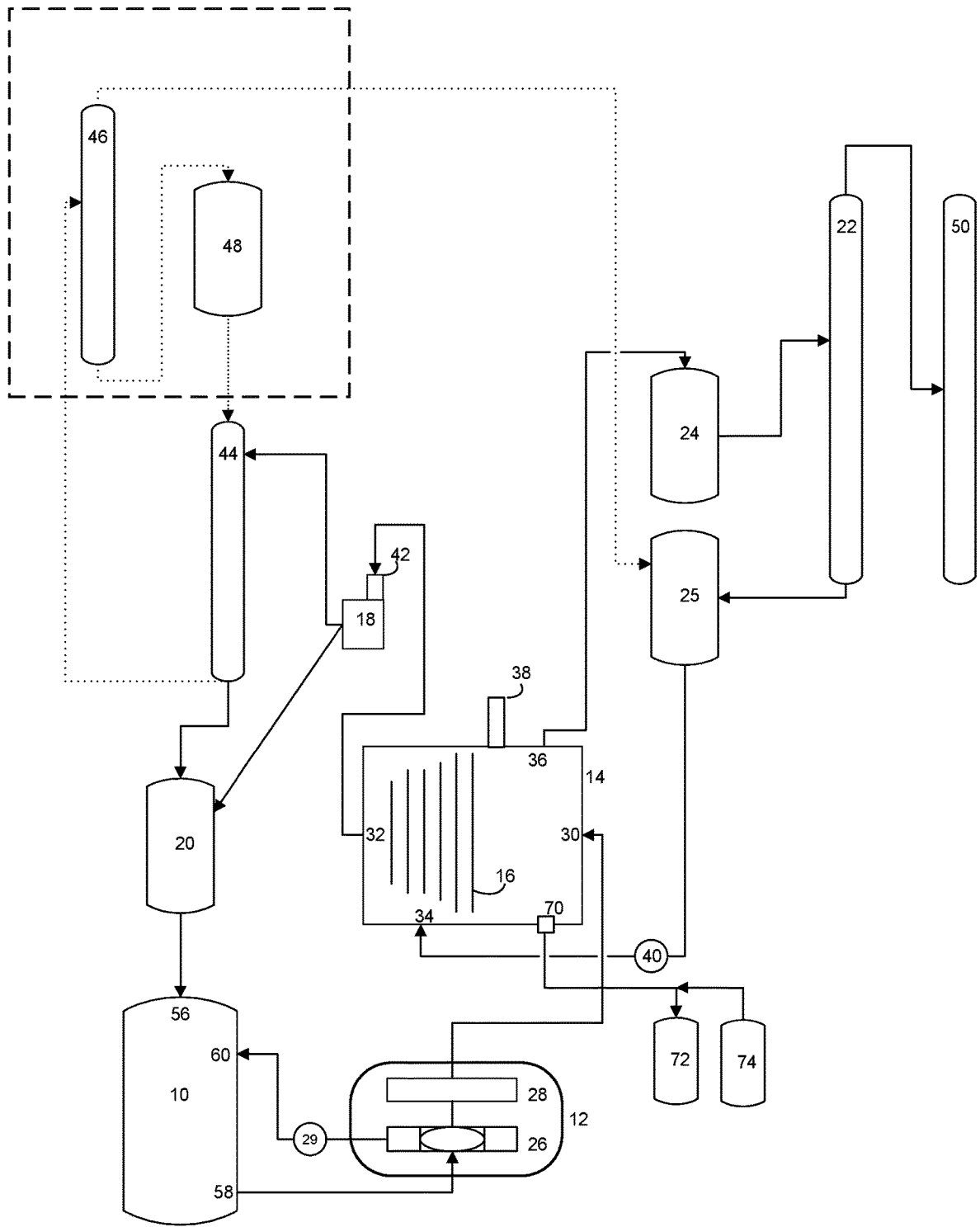

SYSTEM AND METHOD FOR EXTRACTING ETHANOL FROM A FERMENTATION BROTH

CROSS-REFERENCE TO RELATED APPLICATIONS

This application is a divisional of U.S. application Ser. No. 15/325,557 which was a national stage entry of International Application No. PCT/US2015/039849, filed Jul. 10, 2015, which claims the benefit of U.S. Provisional Patent Application No. 62/023,467, filed Jul. 11, 2014, Research for this invention was funded in part by the United States. Department of Energy, grant number DE-FG36-08GO18134, and was part of a joint research agreement with the Minnesota Mining Company (3M) within the meaning of 35 U.S.C. § 103(c).

STATEMENT REGARDING FEDERALLY SPONSORED RESEARCH AND COLLABORATIVE RESEARCH

Research for this invention was funded in part by the United States Department of Energy, grant number DE-FG36-08GO18134, and was part of a joint research agreement with the Minnesota Mining Company (3M) within the meaning of 35 U.S.C. § 103(c).

FIELD OF THE INVENTION

The present invention in related to methods and systems for producing organic molecules, such as ethanol, by fermentation, particularly to methods of recovery of ethanol from a fermentation broth, and still more particularly to recovery of ethanol by partitioning ethanol into an organic solvent across a semipermeable membrane.

BACKGROUND

On a volume basis, alcoholic fermentation represents one of the largest fields of industrial biotechnology being used for production of traditional alcoholic beverages (wine, beer, strong alcoholic beverages, etc.) as well as industrial and fuel ethanol. The feedstock for fermentation is typically a sugar source, such as glucose derived from corn starch or sucrose from sugar beets and sugar cane, which are renewable agricultural crops. Fuel ethanol competes with, or at least functions as supplement to, conventional fossil derived fuels but lacks the environmental impact because no more carbon is emitted into the atmosphere by burning ethanol than was assimilated from the atmosphere by the growing crop. However, to compete with conventional fossil fuels and be more widely adapted, the cost of producing ethanol from renewable crops needs to be reduced and the carbon dioxide emitted by the ethanol production process itself also needs to be reduced to lower the environmental impact.

One of the most costly components of fuel grade ethanol production is the energy required for distillation of the ethanol from the aqueous fermentation broth in which it is made. Typically, the energy used for distillation is obtained from conventional fossil fuels. Therefore, any savings that can be realized from lowering the energy costs incident to distillation will simultaneously lower the cost of ethanol production and the carbon dioxide emissions incident to its production.

One of the reasons distillation costs for ethanol production is high is that water comprising the fermentation broth has one of the highest heat capacities of ethanol miscible liquids. Another reason is that ethanol and water form an azeotrope making it difficult to separate the species efficiently by distillation, especially because their boiling points are only separated by 22° C. It would reduce distillation cost if ethanol could first be extracted from the aqueous fermentation broth into an organic solvent having a lower heat than water, and which has a significantly different boiling point and does not form an azeotrope with ethanol.

Certain selectively permeable membranes have been described that permit preferential passage of organic compounds, such as ethanol relative to water. Examples of such selective membranes have been described in U.S. Pat. Nos. 7,794,593, 7,517,455, 7,105,089 and 7,122,709. It would be beneficial to the field of ethanol production, or more generally to the field of production of any organic molecule by fermentation, if an efficient system could be designed that exploits the selectively permeability of such membranes to transfer the compound from the aqueous fermentation broth into an organic solvent, which would reduce the carbon footprint, cost and energy associated with the manufacturing and separation of organic compounds made by fermentation.

The invention described hereafter provides such a system, particularly exemplified for ethanol manufacturing, but generally applicable to the manufacturing of any organic compound by fermentation where the compound can be extracted across a selectively permeable membrane to separate it from the aqueous fermentation broth.

BRIEF SUMMARY OF THE INVENTION

Described herein is a system and method for producing an organic compound by fermentation that includes a system for extraction of the organic compound from the aqueous fermentation broth into an organic solvent across a semipermeable membrane. The system can be operated in batch at the end of a fermentation or more preferably, continuously during the fermentation process wherein multiple components used in the process, i.e., the fermentation media, the biomass, and the extracting solvent are recycled within the system. The system and method are particularly well adapted and exemplified by producing and extracting ethanol.

With more particularity, described herein is a system for production of an organic compound from a sugar source by fermentation, where the system includes a fermentation vessel for containing a fermentation broth; a solids separation means in fluid connection with the fermentation vessel to receive at least a portion of the fermentation broth wherein said solids separation means is configured to separate suspended solids from the fermentation broth to produce a clarified broth. Solids in the fermentation media include the biomass and may include other non-solubilized material such as grain particles. The solids separation means is configured to conduct a flow of the clarified broth out of the separation means. A membrane module is configured to receive the flow of clarified broth, wherein said membrane module includes a selectively permeable membrane configured to permit preferential passage of the organic compound relative to water. The membrane module includes: a broth inlet port to receive the flow of clarified broth from the solids separation means in a first flow direction tangential to the membrane; a broth exit port to conduct a flow of solvent-extracted broth comprising residual extraction solvent from the membrane module; a solvent inlet port to receive a flow of an extraction solvent in a second flow direction tangential to the membrane; an outlet port configured to conduct the flow of extraction solvent containing the organic compound from the membrane module; and, a pressurizing means to maintain a positive pressure on the flow of clarified broth relative to the flow of extraction solvent in the membrane module. The pressurizing means may further include a vent for releasing carbon dioxide contained in the clarified broth from the membrane module.

The system may further include a decanter configured to receive the flow of solvent-extracted broth from the membrane module and to separate an extraction solvent phase comprising a portion of said residual extraction solvent from an aqueous phase of the solvent-extracted broth. The decanter may further be configured to return the aqueous phase to the fermentation vessel.

In certain embodiments the separation means comprises a filtration apparatus and in some embodiment, a plurality of the filtration apparatus. In desirable embodiments the filtration apparatus is configured with a means to return at least a portion of the separated suspended solids to the fermentation vessel. In exemplary embodiments the filtration apparatus is an ultrafilter.

In other embodiments the solids separation means comprises a centrifuge. In exemplary embodiments the centrifuge is a continuous flow centrifuge. The continuous flow centrifuge may further be configured with a means to return at least a portion of the separated suspended solids to the fermentation vessel. Embodiments where the solids separation means includes a centrifuge may also be combined with a solids separation means that additionally comprises a filtration apparatus.

Typically the suspended material entering the system comprises a residual amount of the fermentation broth and the solids separation means is configured with a means to separate the suspended solids from the residual fermentation broth.

The fermentation vessel used in the system should include a first fermenter inlet port for receiving a flow of carbohydrate feed stock into the vessel; a second fermenter inlet port for receiving the flow of the solvent extracted broth into the fermentation vessel; and a fermenter exit port configured to conduct a portion of the fermentation broth from the fermentation vessel to the solids separation means. The system may further include a third fermenter inlet port configured for receiving the separated solids. In certain embodiment of the system the fermentation vessel comprises a cascading train of a plurality of fermentation vessels linked in series.

The system typically may include a pump operably connected to the membrane module to increase a rate of flow of the extraction solvent within said module relative to a rate of the flow of the extraction solvent into and out of said membrane module. An expanded system may further include a distillation apparatus configured to receive the flow of extraction solvent from the membrane module and to separate the extraction solvent from the organic compound by distillation. In ideal embodiments the system is further configured to return the distilled solvent from the distillation apparatus to the flow of extraction solvent into the membrane module.

The system may further include a separation enhancing means operably connected to the decanter to slow the rate of the flow of solvent-extracted broth and thereby enhance separation of the extraction solvent phase from the aqueous phase. In an exemplary embodiment, the separation enhancing means is a vertical tube having an increased diameter over a tube feeding into the vertical tube. The system may further include a settling tank between the decanter and the fermentation vessel.

In some embodiments the system may include a liquid/liquid extraction module in fluid communication with the decanter and configured to receive the solvent-extracted broth and to contact the solvent-extracted broth with a second extraction solvent that preferentially partitions the residual extraction solvent into a second extraction solvent phase relative to the aqueous phase. In such embodiments the system may further comprise a second distillation apparatus configured to receive the second extraction solvent phase and separate the membrane module extraction solvent from the second extraction solvent. The distillation apparatus can be configured to return the membrane module extraction solvent to the flow of extraction solvent into the membrane module and return the second extraction solvent to the liquid/liquid extraction module. In certain embodiments, the liquid/liquid extraction module is further configured to return the aqueous phase to the fermentation vessel.

In exemplary embodiments the organic compound is ethanol and the membrane module extraction solvent comprises a solvent selected from the group consisting of dodecane and 2,4, dimethylheptanol. In these embodiments, the second extraction solvent may comprises dodecane.

In another aspect the forging embodiments of the system are employed in a method of making an organic compound by fermentation, which includes fermentation with an organism that makes the organic compound in a system as described herein; and collecting the organic compound. In the exemplary embodiment the organic compound is ethanol, the membrane module extraction solvent comprises a solvent selected from the group consisting of dodecane and 2,4, dimethylheptanol, and the second extraction solvent comprises dodecane.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 1 is a schematic diagram of one embodiment of the system of the present invention.

DETAILED DESCRIPTION

Described herein is a system and method for producing an organic compound using fermentation wherein multiple components of the system are recycled within the system. The system and method allow for extraction of a high concentration of the organic compound from the fermentation broth in a batch or preferably in a continuous flow system that allows recycling of the biomass, aqueous fermentation broth and extraction solvents simultaneously during the fermentation. The system and method are particularly well adapted for producing and extracting ethanol.

One embodiment of the present invention is as depicted in FIG. 1. The system comprises a fermentation vessel 10 for containing a fermentation broth in fluid communication with a solids separation means 12, which receives at least a portion of the fermentation broth. The solids separation means is configured to separate the suspended solids (i.e., biomass and/or unsolubilized material such a grain particles)

from the fermentation broth to produce a clarified broth and conduct a flow of the clarified broth out of the separation means 12.

The clarified broth exiting the solids separation means 12 is received by a membrane module 14 comprising a selectively permeable membrane 16 configured to permit preferential passage of the organic compound across the membrane and into an extracting solvent relative to water. The flow of solvent-extracted broth from the membrane module 14 travels to a decanter 18 in fluid communication with the membrane module 14. The decanter 18 is configured to separate residual water that does cross the membrane from the extraction solvent. The aqueous phase of the solvent-extracted broth may likewise be passed through a settling tank 20 to separate residual extracting solvent from that passes into the broth from the aqueous phase before returning the aqueous phase to the fermentation vessel 10.

The flow of extraction solvent with the extracted organic compound exiting membrane module 14 is received by a holding vessel 24 before entering a distillation apparatus 22 configured to receive the extracted mixture and separate the extraction solvent from the organic compound by distillation. The organic compound is collected, and the distilled membrane module extraction solvent is preferably recycled to the flow of extraction solvent into membrane module 14. The distilled solvent may be held in a membrane extraction solvent storage tank 25 before being returned to membrane module 14.

Having generally described one embodiment of the present invention, additional details of certain elements of the system in certain embodiments of the invention are now described.

The fermentation broth is preferably drawn from fermentation vessel 10 during the optimum production rate of the organic compound. In certain embodiments, including when the organic compound is ethanol, the fermentation broth is preferably removed from fermentation vessel 10 when production of the organic compound is 1-5 g/L/hour, commonly when production is 2-3 g/L/hour. Pulling off the fermentation broth at such times maximizes the efficiency of product output and system throughput. Further, continuously removing and extracting a portion of the organic compound from the fermentation broth prevents the organic compound from building up in the fermentation vessel to a level where it poisons the fermentation organism, thereby allowing the fermentation to be conducted at an optimal rate without slowing down for an indefinite period of time.

The solids separation means 12 is configured to separate the suspended solids from the fermentation broth to form a clarified fermentation broth. Removal of suspended solids from the fermentation broth is important to prevent fouling of the selectively permeable membrane 16 in the membrane module 14, which is very important to enable the system to run in a continuous process. Removal of the suspended solids allows for improved solvent extraction of ethanol and improved selectivity and flux of ethanol-solvent mixture across the membrane 16. A solids separation means 12 is particularly important when the system is used in a dry grind process where the whole corn kernel is saccharified to release soluble glucose from starch because of the large amount of fines in the form of insoluble fiber and germ tissue that would foul the membrane module 14 if not adequately removed. In certain embodiments, the suspended solids content in the fermentation broth exiting the fermentation vessel 10 is 1.0-1.5 w/w. Suspended solids include cell biomass, and in a dry grind process include grain particles and other solid elements present in the fermentation broth as a result of the fermentation process.

In certain embodiments, the system and solids separating means 12 are preferably configured to return all, or more preferably, a portion of the suspended solids to the fermentation tank. By separating the suspended solids, including the fermentation organism, from the broth prior to ethanol extraction, and returning at least a portion of the material to the fermentation vessel, an optimally productive level of the fermentation organism and solid material can be maintained in the system. The suspended solids removed from the fermentation broth typically contain some residual fermentation broth. The residual fermentation broth can be separated from the suspended solids and be returned to fermentation vessel 10 and the separated portion of the suspended solids may be used for other purposes—such as being dried to form an animal feed ingredient.

In certain embodiments, the fermentation organism is a flocculating strain of yeast. In some other embodiments, a flocculent, preferably a divalent cation that induces yeast flocculation, such as Zn, Mg or Mn, is used in the fermentation broth. Flocculation of the fermentation organism can assist in separation of the yeast cells from the fermentation broth.

The suspended solids may be removed from the fermentation broth by any suitable means known in the art for solid/liquid separation, including, but not limited to a means for one or more of sedimentation, centrifugation, or other solids concentrating steps, such as filtration. The solids separation means 12 preferably comprises at least one solid/liquid separation device and preferably comprises a series of solid/liquid separation devices.

In certain embodiments the solids separation means 12 comprises a centrifuge 26, preferably a continuous flow centrifuge configured with a means to return at least a portion of the suspended solids containing the fermentation organism to the fermentation vessel 10. Typically such means are a conduit which may preferably be put into fluid communication with a separate pump 29 to return the suspended solids or portion thereof to the fermentation vessel.

In certain embodiments, the solids separation means 12 comprises one or more filtration apparatus 28 to separate the suspended solids from fermentation broth and preferably return at least a portion of the suspended solids to the fermentation vessel 10. At least one filtration apparatus 28 preferably comprises an ultrafilter, such as an ultrafilter bag. The ultrafilter is preferably a 1-2μ filter. Other filtration apparatus known in the art or hereafter developed may be employed consistent with the present invention.

In certain embodiments the solids separation means 12 comprises at least one centrifuge 26 in fluid communication with at least one filtration apparatus 28. The filtration apparatus may be placed between fermentation vessel 10 and the solids separation means 12 and/or between the solids separation means 12 and the membrane module 14. In some embodiments, one, two, three or more of filtration apparatus 28 is employed in addition to centrifuge 26.

The solid separation means 12 is configured to conduct a flow of the clarified broth out of the separation means. The system is configured to deliver the flow of clarified broth to the membrane module 14, which is configured to receive the flow of clarified broth. The membrane module is configured to extract the organic compound from the clarified fermentation broth. The membrane module comprises a selectively permeable membrane 16 that permits preferential passage of the organic compound relative to water and thus relative to the aqueous fermentation broth. Membranes suitable for use with the present invention are described in U.S. Pat. Nos. 7,794,593, 7,517,455, 7,105,089 and 7,122,709, which are incorporated by reference with respect to such disclosure. Extraction of the organic compound from the fermentation broth through permeable membrane 16 is aided by a suitable extraction solvent. In certain embodiments, the membrane module extraction solvent comprises a solvent selected from the group consisting of dodecane and 2,4, dimethylheptanol. In one preferred embodiment the membrane module extraction solvent comprises 2,4, dimethylheptanol. In some embodiments heat is added, preferably through a heat exchanger, to improve solvent extraction.

In certain embodiments of the invention, on one side of permeable membrane 16, the membrane module 14 comprises a broth inlet port 30 to receive the flow of clarified broth from the solids separation means 12 in a first flow direction tangential to membrane 16 and a broth exit port 32 to conduct a flow of solvent-extracted broth out of membrane module 14. On the other side of selectively permeable membrane 16, the membrane module 14 comprises a solvent inlet port 34 to receive a flow of an extraction solvent in a second flow direction tangential to membrane 16 and a solvent outlet port 36 configured to conduct the flow of extraction solvent containing the organic compound from membrane module 14. The clarified broth flow and the extraction solvent flow are on opposite sides of the selectively permeable membrane and the direction of the two can be countercurrent or cross current in relation to each other. Countercurrent is defined herein as a flow of two liquids that are moving in the opposite direction of each other at an angle of 180°. Cross-current is defined herein as a flow of two liquids that are moving in a direction from each other at an angle ranging from >90° to <180°.

The system of the present invention includes a pressurizing means 38 to maintain the pressure of the clarified broth higher relative to pressure of the extraction solvent in membrane module 14. Pressurizing means 38 may be part of the membrane module or operably connected to membrane module 14. Pressurizing means 38 may comprise a valve 38 or series of valves operably connected to membrane module 14 to regulate the flows within membrane module 14 to achieve the desired pressure differential. The pressurizing means preferably comprises a control system for maintaining a constant pressure differential, comprising a programmable logic control (PLC) system operably connected to one or more automatic valves for pressure differential control.

The pressure differential produced by the pressurizing means is necessary to prevent the extraction solvent from passing through selectively permeable membrane 16 and contacting the fermentation broth. Thus, the pressure is higher on the broth side of membrane module 14. In certain preferred embodiments the pressure differential across selectively permeable membrane 16 is between 0.5 and 10 psi, between 0.5 and 7.5 psi, or between 0.5 and 5.0 psi. In some embodiments the pressure differential is 1 psi. Even with a positive pressure differential, some of the extraction solvent may pass through membrane 16 into the filtration broth. In some embodiments the pressure is selected so that the concentration of this residual extraction solvent in the solvent-extracted fermentation broth exiting membrane module 14 is no more than about 100-400 ppm.

All or a portion of pressurizing means 38 may comprise a means for controlling the pressure differential in the membrane 16. Carbon dioxide is present in the fermentation broth as a result of the fermentation process. However, if allowed to build up, the carbon dioxide displaces a sufficient amount of the fermentation broth to create a higher pressure outside of the desired ranges. Pressurizing means 38 may comprise a vent for controlling the release of carbon dioxide to assist in maintaining the desired pressure differential and prevent membrane 16 from rupturing. In some embodiments the vent comprises a liquid column. In some embodiments the vent comprises a "T" fitting installed on top of membrane module 14 with a standpipe attached to allow carbon dioxide to vent from the fermentation broth. The T may be attached to the membrane module via multiple taps in a top Plexiglas cover of membrane module 14. The venting of $CO_2$ further maintains a higher concentration of broth in membrane module 14, which allows a higher mass transfer across selectively permeable membrane 16.

In certain embodiments, the system of the present invention further comprises a pump 40 operably connected to membrane module 14 to increase the rate of the flow of extraction solvent within module 14 relative to the rate of the flow of the extraction solvent into and out of the membrane module. Pump 40 recirculates the extraction solvent within membrane module 14, resulting in an extraction solvent flow rate within module 14 that can be greater than 10 times the rate of the incoming fresh extraction solvent and the outgoing spent extraction solvent containing the organic compound. This increased flow rate adds turbidity to the laminar flow along membrane 16, effectively reducing the boundary layer thickness at the face of membrane module 14. This increases the miscibility of the organic compound into the extraction solvent and produces a higher transfer rate of the organic compound into the extraction solvent. Preferably the flow rate into and out of membrane module 14 is 1-1.5 L/minute. Preferably the flow rate of the extraction solvent within membrane module 14 is 15-20 L/minute, or 1 gal/min/sq. ft.

In certain embodiments, the membrane module is configured with clean-in-place valves 70 which include drain valves, shut off valves and cleaning valves to allow a clean-in-place process for cleaning membrane module 14. The cleaning process removes biofilm from membrane 16 that would impede flow through membrane 16 if allowed to accumulate. The clean-in-place process is preferably run with a frequency to maintain a desired flow rate through the membrane, preferably at least once a week. The shut off valves, when closed, block flow into and out of membrane module 14 through of the broth inlet and exit ports 30 and 32 and the solvent input and outlet ports 34 and 36. The drain valves, when open, allow the contents of membrane module 14 to drain into a collection tank 72. The cleaning valves are operably connected to tanks holding cleaning solutions 74 and when open, allow a cleaning solution to enter the membrane module. The cleaning solution preferably comprises a 1 to 2N sodium hydroxide solution and a Polysorbate 60 surfactant. To clean membrane module 14, the broth inlet and solvent input shut off valves are closed and the extraction solvent is allowed to exit module 14. The broth exit and solvent outlet ports are then closed. The cleaning valves are opened to allow the cleaning solution to enter the membrane module. The drain valves and cleaning valves are operated to maintain a flow rate of cleaning solution favorable for cleaning membrane module 14. After cleaning, the cleaning valves are closed and the broth inlet and solvent input ports 30 and 34 are opened for sufficient time to push out any remaining cleaning solution through the drain valves. The drain valves are then closed and the broth exit and solvent outlet ports 32 and 36 are opened to return membrane module 14 to normal operations.

In certain embodiments, the broth exit port 32 of membrane module 14 is in fluid communication with one or more liquid/liquid separation means configured to separate from the solvent-extracted broth any extraction solvent that leaked into the broth. If not removed, the residual extraction solvent can kill the fermentation organism when the broth is returned to the fermentation vessel 10. Preferably the concentration of solvent in the broth is reduced to less than 400 ppm, more preferably less than 100 ppm. In some embodiments, the liquid/liquid extraction means comprises one or more decanters 18. The decanter is preferably a horizontal decanter without a centrifuge. The extraction solvent separates out of the aqueous broth phase and into an upper extraction solvent phase within the decanter. The decanter is further configured to return the aqueous broth phase to fermentation vessel 10. In such embodiments, the system may be configured with a settling tank 20 between the decanter 18 and the fermentation vessel 10. Settling tank 20 is preferably a gravity separation vessel that allows any residual lower density extraction solvents to separate and be decanted from the higher density broth returning to the fermentation vessel out of the bottom of tank 20.

In certain embodiments, horizontal decanter 18 is operably connected to a separation enhancing means 42 configured to increase the residence time of the solvent-extracted liquid in the system during separation of the module membrane extraction solvent from the aqueous solvent-extracted broth. Preferably the separation enhancing means is a vertical tube located between the membrane module and the decanter having an increased diameter relative to the tube feeding into the separation enhancing means 42. The increase in diameter slows the rate of the flow of the solvent-extracted broth, allowing more time for the solvent to rise to the top and the broth to separate out at the bottom. In certain preferred embodiments the increase in diameter is between 1.5 and 2.0 inches.

In certain embodiments, the system further comprises a liquid/liquid extraction module 44, preferably located between the decanter and the fermentation vessel. Liquid/liquid extraction module 44 comprises a means to contact the solvent-extracted broth with a second extraction solvent that preferentially partitions any residual membrane module extraction into a second extraction solvent phase relative to the aqueous phase of the fermentation broth. The liquid/liquid extraction module preferably comprises of counter current extraction with the second extraction solvent moving in a direction opposite to the direction of the solvent extracted broth, both moving in a vertical direction. The second extraction solvent preferably comprises a solvent selected from the group consisting of dodecane and 2,4, dimethylheptanol. In one preferred embodiment the second extraction solvent comprises dodecane.

In certain embodiments the liquid/liquid extraction module is further configured to return the aqueous broth phase to the fermentation vessel either directly or via the settling tank and/or other liquid/liquid separation means. In certain embodiments, the system of the present invention further comprises a second distillation apparatus 46 configured to receive the second extraction solvent phase and separate the membrane module extraction solvent from the second extraction solvent. The membrane module extraction solvent is preferably returned to the flow of extraction solvent into membrane module 14, preferably via solvent storage tank 25 and the second extraction solvent is preferably returned to the liquid/liquid extraction module 44, preferably via second solvent storage tank 48.

In certain embodiments, the organic compound collected from first distillation apparatus 22 is collected as vapor off the top of the distillation apparatus and is sent to a secondary high vacuum distillation apparatus 50 in which the organic compound is further concentrated. In some embodiments, the high vacuum is maintained by a liquid ring vacuum pump system, a dry ring vacuum pump system or a steam injector, each of which removes non-condensable gasses from the apparatus. In some embodiments, a continuous stable vacuum is supplied to the secondary high vacuum distillation apparatus by a dedicated liquid ring vacuum pump.

In certain embodiments the fermentation vessel 10 comprises a plurality of fermentation vessels arranged in a cascading train.

In certain embodiments, fermentation vessel 10 comprises a first fermenter inlet port for receiving a flow of carbohydrate feed stock into the vessel, a second fermenter inlet port 56 for receiving the flow of the solvent extracted broth into the fermentation vessel 10, and a fermenter exit port 58 configured to conduct a portion of the fermentation broth from fermentation vessel 10 to solids separation means 12. The fermentation vessel preferably includes a third fermenter inlet port 60 configured for receiving the separated suspended solids, including the separated fermentation organism from solids separation means 12. Fermentation vessel 10 preferably includes a piping network and venting system that draws off fermentation vapor to the atmosphere. A fan may be operably coupled to the venting system to assist in drawing off the vapor.

In certain embodiments, the membrane module solvent is a green solvent, i.e., a solvent that can be produced form a renewable feedstock, to enhance recovery of the organic compound from the fermentation broth. In some embodiments the green solvent is produced in a yeast fermentation process. Green solvents consistent with the present invention may be selected from the group consisting of alcohols present in fusel oils or ethyl esters of organic acids. Alcohols present in fusel oils include amyl alcohols and propyl alcohols. Ethyl esters of organic acids include ethyl acetate, ethyl lactate, and ethyl propionate. Other suitable green solvents include fatty acid methyl esters of biodiesel. Green solvents are less toxic to fermentation organisms than other organic solvents, such as dodecane and 2,4, dimethylheptanol.

In certain embodiments, the system comprises a PLC system control system for regulating various flows throughout the system.

The present invention further comprises a method of making an organic compound by fermenting a carbohydrate source with a fermentation organism that makes the organic compound using the system of the present invention and collecting the organic compound. The method is particularly well-suited for making ethanol.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A method of making an organic compound by fermentation, comprising;

fermenting a carbohydrate source with a fermentation organism that makes the organic compound in a fermentation vessel forming a fermentation broth comprising suspended solids and the organic compound;

passing a portion of the fermentation broth to a solids separation means in fluid connection with the fermentation vessel to separate suspended solids from the fermentation broth forming a clarified broth;

passing a flow of the clarified broth through a membrane module comprising a selectively permeable membrane that permits passage of more of the organic compound relative to water across the membrane in a first flow direction tangential to the surface of the membrane:

passing a flow of organic extraction solvent through the membrane module to contact the membrane on a side opposite the side receiving the flow of clarified broth in a second flow direction tangential to the membrane that is countercurrent or cross current relative to the flow of clarified broth in the first direction while maintaining a positive pressure on the flow of clarified broth relative to the flow of extraction solvent in the membrane module, thereby forming a solvent extract containing a portion of the organic compound and a solvent extracted broth containing a portion of the organic solvent;

passing the solvent-extracted broth from the membrane module to a decanter to separate the solvent extracted broth into a solvent phase comprised of the organic solvent and an aqueous phase, wherein passing the solvent extracted broth to the decanter includes slowing the rate of flow of the solvent extracted broth from the membrane module to thereby enhance separation of into the solvent phase and the aqueous phase in the decanter;

passing the aqueous phase from the decanter back to the fermentation vessel;

passing the solvent extract from the membrane module to a separation means to separate the organic compound from the extraction solvent; and collecting the organic compound.

2. The method claim 1, wherein the organic compound is ethanol.

3. The method of claim 1, wherein the extraction solvent comprises a solvent selected from the group consisting of dodecane and 2,4, dimethylheptanol.

4. The method of claim 2, wherein the extraction solvent comprises dodecane.

5. The method of claim 1 wherein the solids separation means comprises a filtration apparatus.

6. The method of claim 1 further comprising returning the separated solids to the fermentation vessel.

7. The method of claim 1 wherein the flow of clarified broth flows is countercurrent direction relative to the flow of extraction solvent.

8. The method of claim 1 wherein low of clarified broth flows is cross current relative to the flow of extraction solvent.

9. The method of claim 1 wherein the organic compound is separated from the extraction solvent by distillation.

10. The method of claim 1 wherein the extraction solvent separated from the organic compound is returned to the flow of extraction solvent passed to the membrane module or to a vessel containing the extraction solvent from which extraction solvent is passed through the membrane module.

11. The method of claim 1 wherein the solvent phase separated in the decanter is returned to the flow of extraction solvent passed to the membrane module or to a vessel containing the extraction solvent from which extraction solvent is passed through the membrane module.

* * * * *